(12) United States Patent
Volgyesi

(10) Patent No.: US 6,857,443 B2
(45) Date of Patent: Feb. 22, 2005

(54) ELECTRONIC GAS BLENDER AND GAS FLOW CONTROL MECHANISM THEREFOR

(76) Inventor: George A. Volgyesi, 36 Gatehead Road, Toronto Ontario (CA), M2J 2P5

( * ) Notice: Subject to any disclaimer, the term of this patent is extended or adjusted under 35 U.S.C. 154(b) by 83 days.

(21) Appl. No.: 10/370,768

(22) Filed: Feb. 24, 2003

(65) Prior Publication Data

US 2004/0163706 A1 Aug. 26, 2004

(51) Int. Cl.$^7$ ............................................. G05D 11/13
(52) U.S. Cl. .................. 137/101.19; 137/607; 137/898
(58) Field of Search ........................... 137/88, 93, 100, 137/101.19, 607, 898; 138/40; 251/118

(56) References Cited

U.S. PATENT DOCUMENTS

| | | | | |
|---|---|---|---|---|
| 3,556,157 A | * | 1/1971 | Eckerlin et al. ............... | 138/46 |
| 3,593,735 A | * | 7/1971 | Reiher .......................... | 137/88 |
| 3,841,560 A | * | 10/1974 | Sielaff ......................... | 239/136 |
| 4,602,653 A | * | 7/1986 | Ruiz-Vela et al. ............ | 137/88 |
| 4,605,034 A | * | 8/1986 | Urushida ...................... | 137/88 |
| 5,205,322 A | * | 4/1993 | Merick et al. ............... | 137/597 |
| 5,722,449 A | * | 3/1998 | Heinonen et al. ...... | 137/101.19 |
| 5,887,611 A | * | 3/1999 | Lampotang et al. .......... | 137/93 |

FOREIGN PATENT DOCUMENTS

| | | |
|---|---|---|
| EP | 0 597 374 A1 * | 11/1993 |
| GB | 2 136 703 A * | 9/1984 |

* cited by examiner

Primary Examiner—Ramesh Krishnamurthy
(74) Attorney, Agent, or Firm—Riches, McKenzie & Herbert LLP; Paul Herbert

(57) ABSTRACT

A gas flow control mechanism for a gas blender comprising: a voltage sensitive orifice defining a passage for each gas to be controlled and having an inlet port in fluid communication with a gas source and an outlet port in fluid communication with a plenum for mixing at least two gases; a gas flow controller placed in a feed back loop to adjust at least a parameter or characteristic of a gas flow exiting from the orifice through the outlet port to preset value; the gas flow controller comprising a gas flow resistor in fluid communication with the gas exiting from the orifice and adapted to generate an output signal based on a gas flow characteristic, and a comparator, responsive to the gas resistor flow signal, to continuously evaluate and monitor the characteristic of the gas exiting from the orifice, compare the same with the preset value and minimize any difference therebetween by adjusting current supplied to the orifice which in turn adjusts the gas flow therethrough to the preset value by adjusting the passage.

8 Claims, 12 Drawing Sheets

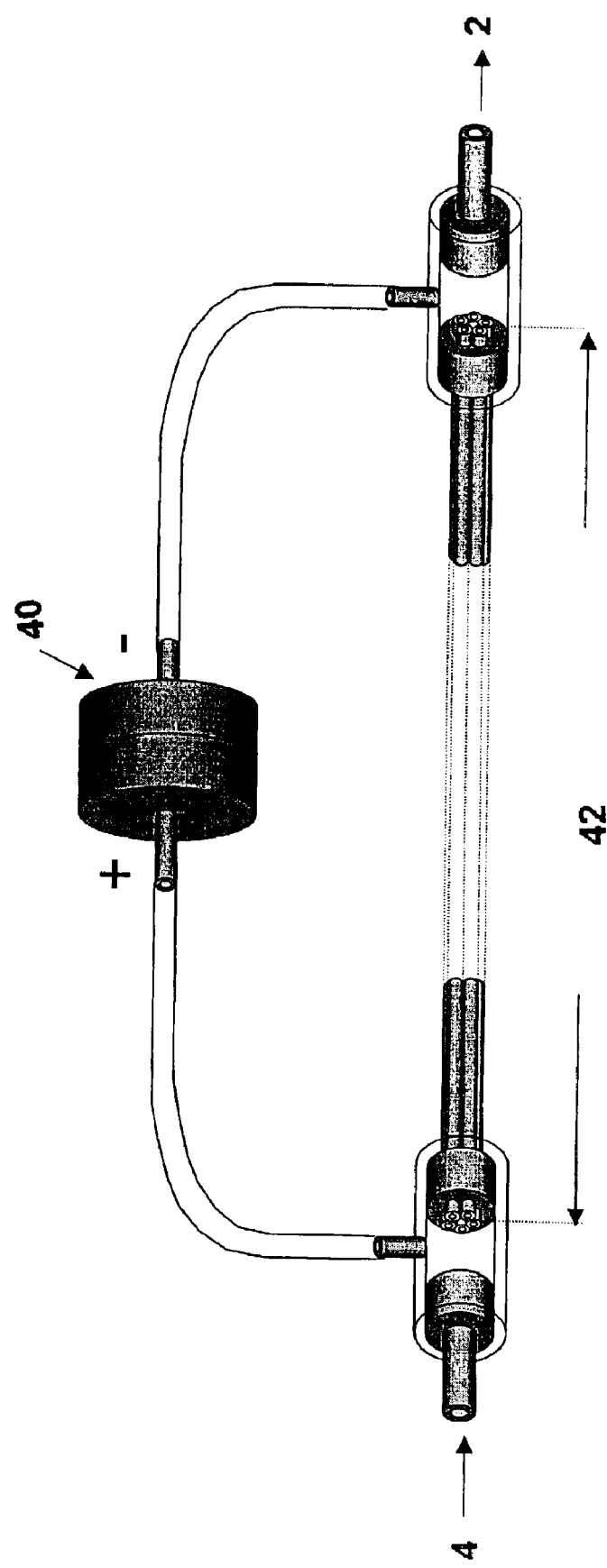

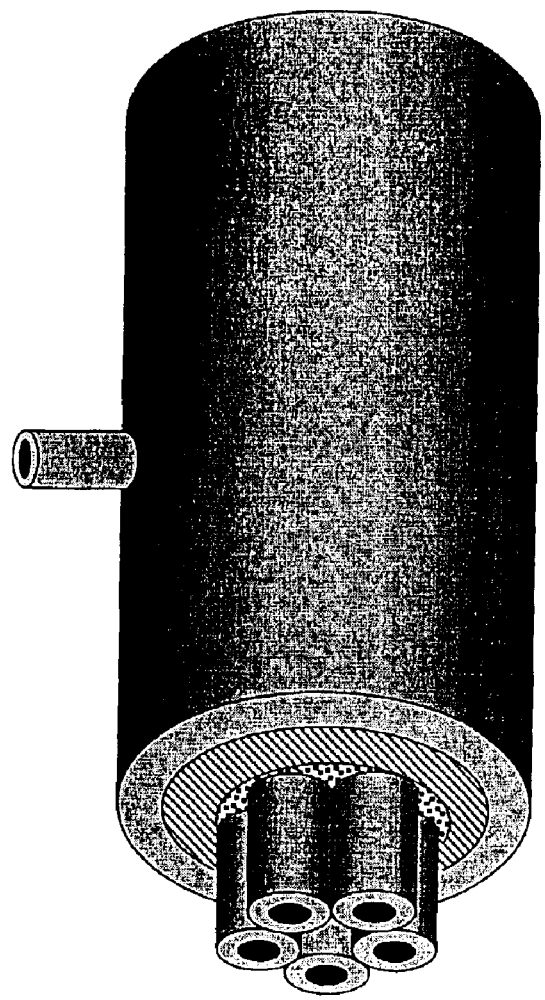
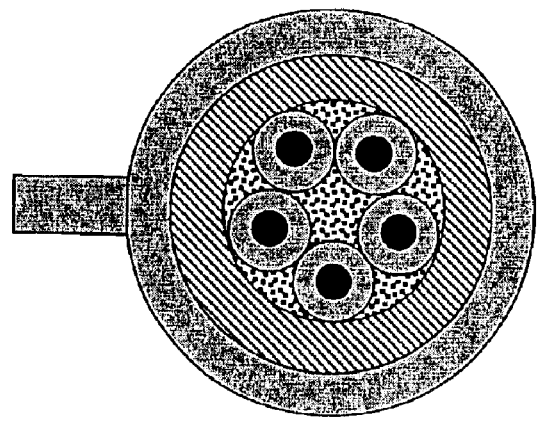
FIGURE 8B

ELECTRONIC GAS BLENDER AND GAS FLOW CONTROL MECHANISM THEREFOR

BACKGROUND OF THE INVENTION

This invention relates to improvements in or relating to electronic gas blenders in general and is particular to electronic gas blenders for medical applications such as surgical operations, ventilation, and the like, and gas flow control mechanisms therefor.

Traditionally, in medical applications, the flows of oxygen, air and nitrous oxide are manually controlled by means of calibrated rotameters with their associated needle valves.

During surgical operations, the anesthesiologist sets the flow of each gas to deliver an appropriate total flow with the desired oxygen concentration. The oxygen concentration is usually monitored by means of an oxygen analizer which contains a means for alerting the operator of any dangerously inappropriate conditions. The manual needle valves provide complete control and the rotameters provide visual affirmation of the flow of each gas.

There are several disadvantages to this traditional delivery of gases during surgical operations. To administer the appropriate flow of gases with the desired oxygen and nitrous oxide concentration, the operator has to estimate the flow of each gas manually. If the total flow needs to be changed, each gas flow must be manually re-adjusted. This requires a great deal of mental effort and may be stressful in rapidly changing situations.

An improved method of mixing gases for medical applications utilizes a mechanical blender, like that manufactured by the Bird company (U.S. Pat. No. 3,895,642). Although mechanical blenders are simple and reliable, they have limited accuracy, especially at low flow rates. They are designed to blend two specific gases only, usually air and $O_2$ or $N_2O$ and $O_2$ and therefore a separate blender is needed for each combination of gases. Being mechanical, they also lack any indicators of diminished accuracy and any possibility of automatic documentation of gas flows and/or concentrations.

U.S. Pat. No. 5,887,611 discloses a microprocessor controlled gas-blender, the disclosure of which is incorporated herein by reference. It uses an $O_2$ sensor in a feedback loop to control the gas flows. A major drawback of this device is that it depends entirely on the accuracy of the $O_2$ sensor for its operation. If the $O_2$ sensor fails or becomes inaccurate, the entire system may fail or become inaccurate. Another inherent drawback of this device being microprocessor controlled is the limited resolution of the flow control. A limiting characteristic of microprocessor (digital) operation is that the resolution of flow control is discontinuous. It can only provide a number of discrete steps within its range of control, where the number of steps depends on the precision of the analog to digital conversion. The resolution limitations may also preclude the use of such a blender at lower flows, because its accuracy would be severely degraded.

A more versatile device used for controlling the flow of gases is the Mass Flow Controller (MFC). It is highly accurate, but suffers from several disadvantages. A problem with the MFC is its slow response. Even a faster MFC may require a response time of over a second. This slow response precludes the MFC from use in dynamic situations where a fast response is crucial. In closed-loop feedback applications, the slow response of the MFC causes undesirable effects like "popping" on turn-on (overshoot) and very sluggish response to changes in flow setting. It is also bulky, heavy and relatively expensive.

SUMMARY OF THE INVENTION

An object of the present invention is to avoid, if not minimize, the above mentioned drawbacks.

Another object of the invention is to provide a gas flow control mechanism which may be faster, reliable and less expensive, and an electronic gas blender incorporating such a control mechanism.

It has now been found that a Voltage Controlled Orifice (VCO) valve can conveniently be used as a control device, and it is faster, lighter, smaller and less expensive than the MFC. Its response time is measured in milliseconds, and so it may be nearly three orders of magnitude faster than the MFC. The VCO is therefore far more suitable for closed-loop feedback applications where a fast dynamic response is required.

The control mechanism for a gas blender according to this invention may utilize a VCO valve for each gas to be controlled. It can be used either in an automatic or a manual mode and provides infinitely variable, but independent control of total gas flow and $O_2$ concentration. Another advantage is that a single control mechanism and hence a single blender can be used to blend air and/or $N_2O$ with $O_2$ and can be easily re-adjusted to accommodate any combination of gases. The blender combines the option of the manual control of the traditional anesthesia machine with electronic control and so all flows can be automatically monitored and documented. The electronic design incorporating an analogue computer, enhances the accuracy, reliability and versatility of the device. The blender may preferably incorporate solenoid valves (normally open) in parallel with the VCO valves (normally closed), so that in case of any power failure, the blender may be used completely manually using traditional needle valves and rotameters for adjusting gas flows. This feature also permits the operator to use any of the modes of operation: fully manual (controlling each gas flow independently with individual needle-valves), manual-electronic (controlling each gas flow independently with individual potentiometers) or fully automatic (selecting the gases to be mixed, the total gas flow and the required $O_2$ concentration). In the fully automatic mode, the blender maintains the required total gas flow at any setting of the $O_2$ concentration regardless of changes in gas source pressure variations. The may provide a measure of comfort and gradual training for those who do not yet fully trust technology. This design also ensures that even if the electronic control fails (a worst case), the blender may still be used in the traditional fashion manually. The use of an oxygen monitor, which is now mandatory in many countries, provides an extra measure of safety but is not required for the operation of the blender. Additional alarms may also be used to ensure more safety to the blender.

Thus, according to one aspect of the present invention, there is provided a gas flow control mechanism for a gas blender comprising: a voltage sensitive orifice defining a passage for each gas to be controlled and having an inlet port in fluid communication with a gas source and an outlet port in fluid communication with a plenum for mixing at least two gases; a gas flow controlling means placed in a feed back loop to adjust at least one parameter or characteristic of a gas flow exiting from the orifice through the outlet port to a preset value; the gas flow controlling means comprising: a gas flow resistor in fluid communication with the gas exiting from the orifice and adapted to generate an output signal based on a gas flow characteristic; and a comparing means responsive to the gas resistor flow signal to continuously evaluate and monitor the characteristic of the gas exiting from the orifice, compare the same with the preset value and minimize any difference there between by adjusting current supplied to the orifice which in turn adjusts the gas flow there through to the preset value by adjusting the passage.

According to another aspect of the invention, there is provided a gas flow control mechanism for an electronic gas blender comprising: a voltage sensitive orifice defining a passage for each gas to be controlled and having an inlet port in fluid communication with a gas source and an outlet port in fluid communication with a plenum for mixing at least two gases; and a gas flow controlling means placed in a feed back loop to adjust a gas flow exiting from the orifice to a preset value, comprising: a linear gas flow resistor in fluid communication with the exiting gas flow; a differential pressure transducer placed in a feed back loop for measuring pressure drop across the gas flow resistor; a comparator responsive to a signal generated by the transducer and adapted to continuously monitor and compare the exiting gas flow with the preset value; and an analogue computer to calculate and generate an appropriate voltage signal required to provide the total gas flow and concentration at the preset value.

According to a further aspect of the invention, there is provided a gas flow control mechanism for an electronic gas blender comprising: a voltage sensitive orifice defining a passage for each gas to be controlled and having an inlet in fluid communication with a gas source and an outlet in fluid communication with a plenum for mixing at least two gases; a normally open solenoid valve in parallel connection with the orifice to bypass the orifice; a gas flow controlling means, placed in a feed back loop, to adjust flow of gas exiting from the orifice to a preset value, comprising: a gas flow resistor in fluid communication with the gas exiting from the orifice and adapted to provide a linear flow resistance to the gas traversing there through which is low enough to allow sufficient gas flow at a minimum gas source pressure; a differential pressure transducer placed in a feed back loop to the flow resistor; and a comparator responsive to a signal generated by the transducer and adapted to continuously monitor and compare the exiting gas flow with the preset value; and an analogue computer to calculate and generate an appropriate voltage signal required to provide the total gas flow and concentration at the preset value, and to adjust the current supplied to the orifice to continuously maintain the exiting gas flow substantially at the preset value; and including a needle valve and a rotameter through which the gas exiting from the solenoid valve and the flow resistor traverses before entering the plenum.

The flow control mechanism may work on the following principle:

Let total gas flow=$FL_{TOT}$
$O_2$ flow=$FL_{O2}$
Air flow=$FL_{AIR}$
$O_2$ Conc. (fractional concentration)=$FiO_2$
It is known that:

$$FiO_2=[0.21FL_{AIR}+FL_{O2}]/FL_{TOT}; \text{ and}$$

$$FL_{AIR}=FL_{TOT}-FL_{O2} \qquad 1$$

Therefore $$Fi_{O2}=[0.21(FL_{TOT}-FL_{O2})+FL_{O2}]/FL_{TOT}$$

Solving for $FL_{O2}$ $$FL_{O2}=1.2658FiO2FL_{TOT}-0.2658FL_{TOT} \qquad 2$$

Equation 2 may be written in a more general form as follows:

$$FL_{O2}=K1FiO2FL_{TOT}-K2FL_{TOT} \qquad 2g$$

where K1 and K2 are constants.
For mixing air and oxygen,
K1=1.2658 and
K2=0.2658
Similarly, for mixing nitrous oxide and oxygen,
K1=1
K2=1
By re-calculating the constants K1 and K2 on the above lines, any other combinations of gases could be blended using the mechanism.

BRIEF DESCRIPTION OF THE DRAWINGS

The invention will now be apparent from the following non-limitative description with reference to the accompanying drawings in which:

FIG. 6A is an end elevational view of the gas flow resistor;

FIG. 6B is a plan elevational view of the gas flow resistor;

FIG. 6C is a side view of FIG. 6A;

FIGS. 8A, 8B and 8C show details of a bundle of flow resistor tubes; and

In the figures, the following are the representative descriptions:

Figure 1:
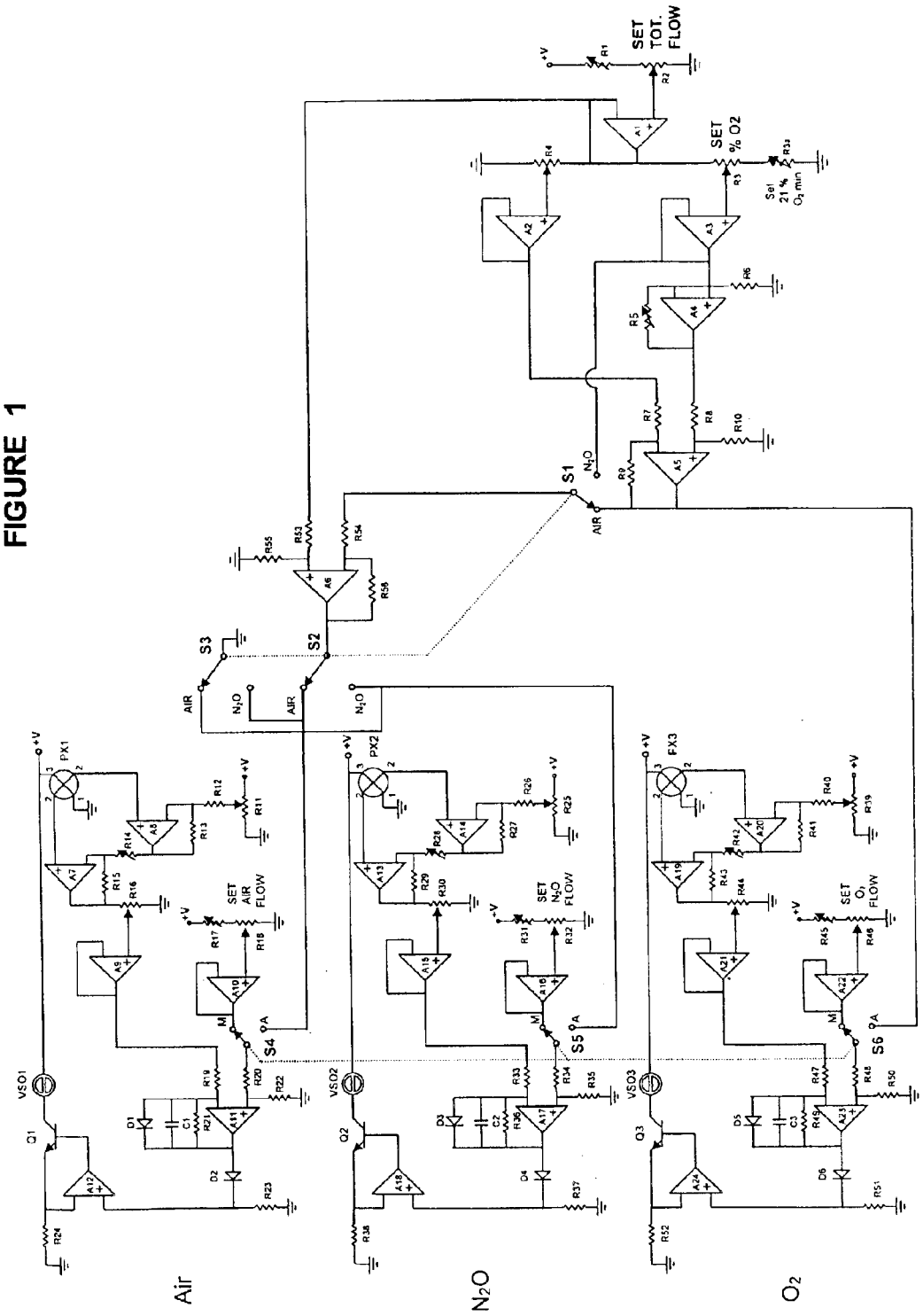
FIGS. 1 and 2 show the electronic circuit diagrams of the gas flow control mechanism for three gases, namely, air, nitrous oxide and oxygen, according to an embodiment of the present invention.

A1–A24 represents ¼ of 324 operational amplifier
PX1–PX3 represents differential pressure transducer (Motorola MPX2200PD)
VSO1–3 represents Voltage Sensitive Orifice (Pneutronics VSONC-5S11)
Q1–Q3 represents Power transistor (2N3055)
D2, D4, D6 represents Germanium diode
D1, D3, D5 represents Silicone diode
S1–S3, S4–S6 represents 3PDT switch
R24, R38, R52 represents 30R, 5W resistors
R1, R3a, R5, R11, R14, R16, R17, R25, R28, R30, R31, R39, R42, R44, R45 represents multi-turn trimmers
2 represents the direction of flow of "gas out"
4 represents the direction of flow of "gas in"
6 represents a rotameter
8 represents a needle valve 10 represents a normally open solenoid valve
12 represents a normally closed solenoid valve
14 represents a flow resistor
16 represents a differential pressure transducer
18 represents a coiled capillary tube bundle
20 represents a connector
22 represents a direction to a differential pressure transducer
24 represents a pressure nipple
26 represents a jacket
28 represents a sleeve
30 represents epoxy
32 represents a capillary tube
34 represents a flared entrance to a capillary tube
36 represents a laminar flow
38 represents a flow channel
40 represents a differential pressure transducer
42 represents the length of the resistance bundle ("L")
44 represents a flow inlet

DETAILED DESCRIPTION OF THE INVENTION

Figure 2:
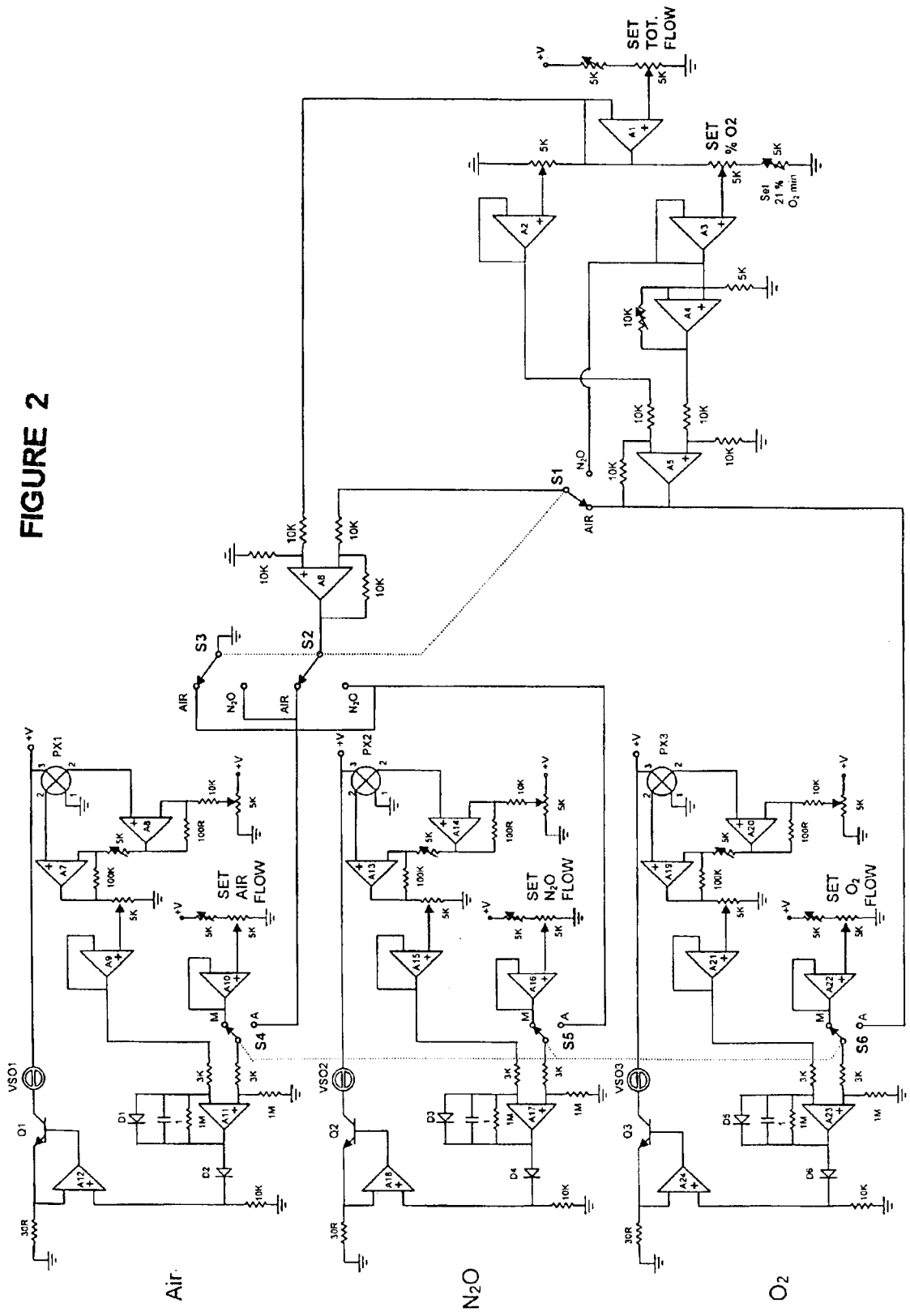

In the electronic circuits shown in FIGS. 1 and 2, the components A1 to A24 are ¼ of 324 operational amplifiers, PX1 to PX3 are differential pressure transducers (Motorola MPX2200PD), VSO1 to VSO3 are voltage sensitive orifices (Pneutronics VSONC-5S11), Q1 to Q3 are power transistors (2N3055), D2, D4 & D6 are germanium diodes, D1, D3 & D5 are silicon diodes, S1 to S3 and S4 to S6 are 3PDT switches, R24, R38 and R52 are 30R, 5W resistors, and R1, R3a, R5, R11, R14, R16, R17, R25, R28, R30, R31, R39, R42, R44 and R45 are 10 multi-turn trimmers.

Equations 1 and 2 given herein above are continuously solved by an analogue computer consisting of operational amplifiers A1 to A6 and associated components.

The total flow is set to the desired value, which is the value that a clinician sets, by adjusting SET TOT.FLOW control knob mechanically coupled to the shaft of R2, and the knob may be located on the front panel (not shown). The range of the total flow is preset by trimpot R1 to correspond to the graduation labels of the total flow control.

The oxygen concentration is set to the desired value, which again is decided by the clinician, by adjusting the SET % $O_2$ control knob mechanically coupled to the shaft of R3 also may be located on the front panel. The trimpot R3a may be preset for a minimum $O_2$ concentration of about 21%. The constants K1 and K2 are set by adjusting trimpots R5 and R4 respectively. The subtraction circuit consisting of A5 and R7 to R10 completes the computation of equation 2 g. Equation 1 is electronically implemented by the subtraction circuit consisting of A6 and R53 to R56.

Switches S1, S2 and S3 are mechanically coupled to actuate synchronously (3PDT) to select the gas (air or $N_2O$ in this case) to blend with $O_2$. This switch also may be located on the front panel.

Figure 3:
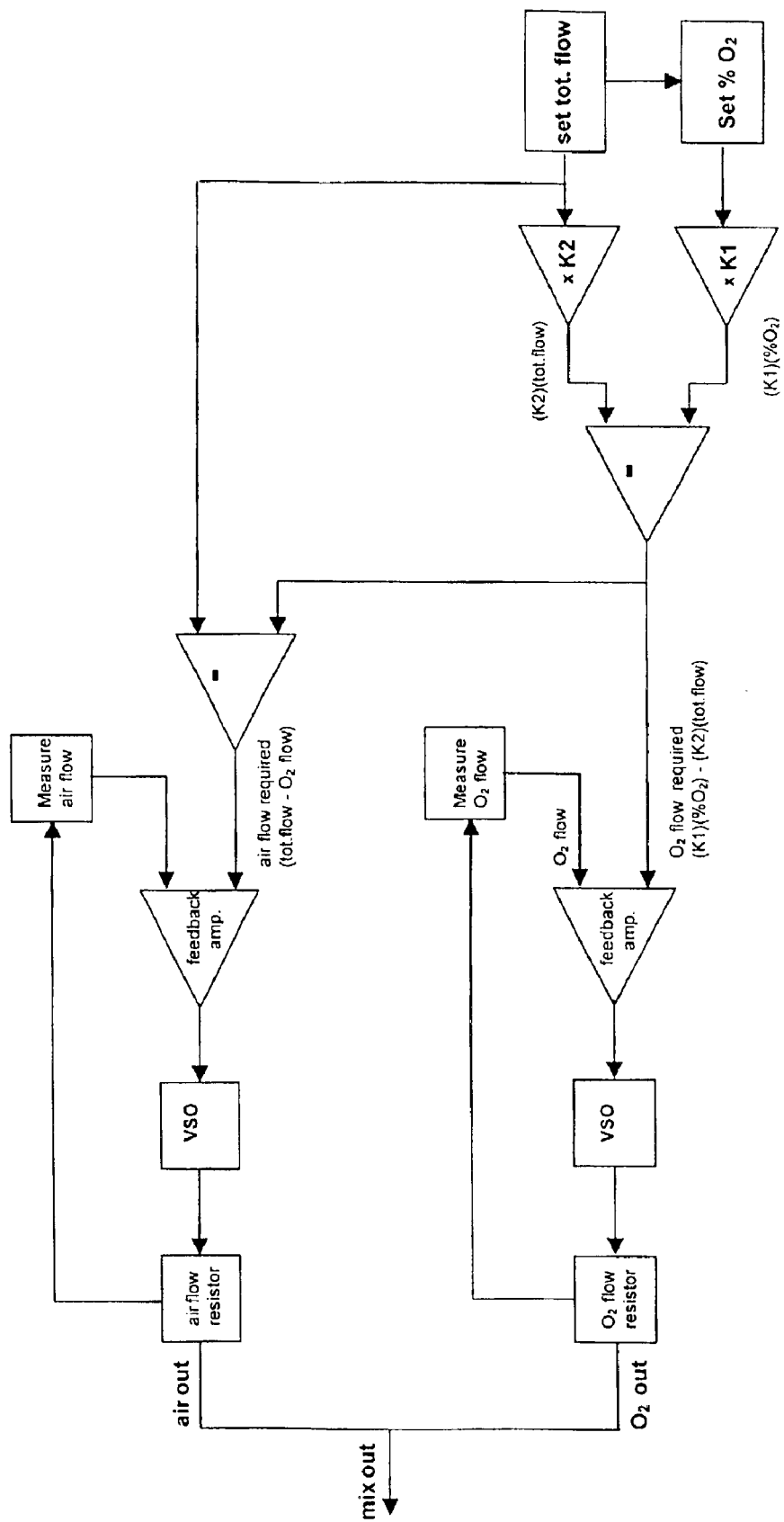
FIG. 3 shows a schematic flow chart for an air-oxygen blender control mechanism.
Figure 4:
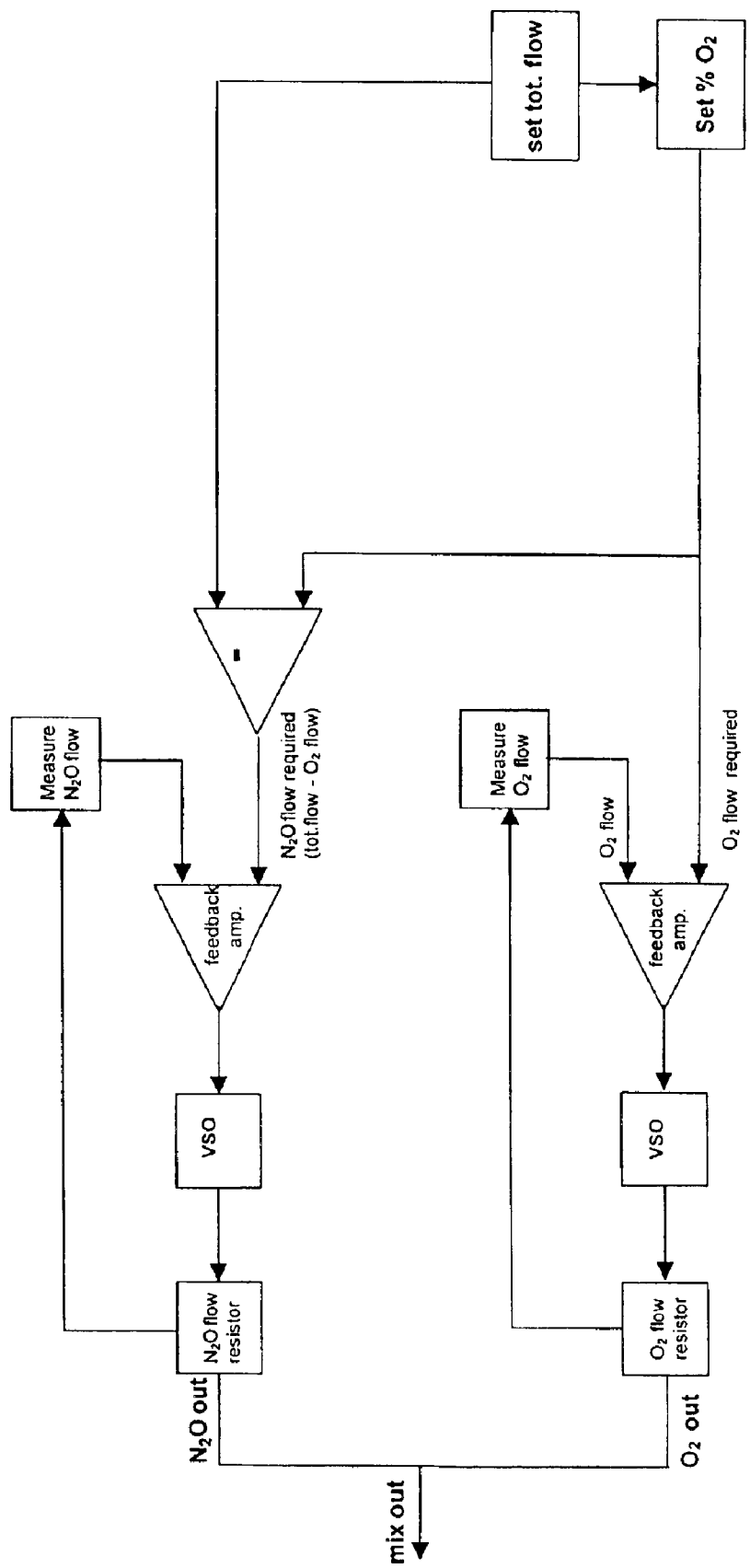
FIG. 4 is similar to FIG. 3 but for a nitrous oxide-oxygen blender.

Because the flow controllers for the three gases are identical, for the sake of convenience, only the $O_2$ flow controller according to an embodiment of this invention will be described herein. The flow controller may consist of a voltage sensitive orifice (VSO3 in FIG. 1) and a flow measuring circuit placed in a feedback loop (see FIGS. 3 and 4), where the VSO3 adjusts the flow to the magnitude required. A voltage signal proportional to the actual flow is obtained by directing the flow through a linear gas-flow resistor (FIGS. 6, 7, 8A, 8B and 8C) and measuring the pressure drop across it. The pressure drop is measured by a differential pressure transducer PX3 (Motorola MPX 2200) and operational amplifiers A19, A20 and A21 (FIG. 1). R39 sets the zero and R42 sets the gain for the pressure transducer.

A high gain difference amplifier A23 continuously compares the actual flow with the required flow and minimizes their difference by adjusting the current supplied to the VSO through the power transistor Q3. The gain of the difference amplifier A23 is determined by the ratio R49/R48. If the gain is too low, the error (the difference between the desired flow and the actual flow) may be too large. If, however, the gain is too high, the circuit may become unstable. The choice of resistances indicated on the circuit diagrams combines good stability with a reasonably small error. The current through VSO3 (and thus the flow of $O_2$) is controlled by the power transistor Q3 which is controlled by A24. R52 determines the maximum current through Q2. The purpose of C3 is to provide stability to the output of A23 by damping. D5 improves the speed of response by preventing the output of A23 from going negative. Diode D6 also prevents Q3 from going into saturation ("latch-up") by allowing only positive excursions from the output of A23 into A24.

The flow channel can be calibrated at a specific known flow by adjusting R42 and R44 to give a specific voltage signal appropriate for that flow (for example 5V=10 L/min).

The blender can be operated either manually or automatically by selecting Auto or Manual setting of the switches S4, S5 and S6, which are ganged together (3PDT). In the manual mode, the flow of each gas is controlled by its manual control potentiometer (i.e., R46, R32 and R18 to set O2, N2O and AIR FLOW, respectively). In the automatic mode, the flow of each gas is automatically controlled by the analogue computer previously described to provide the total flow and oxygen concentration selected by the operator.

The gas to be blended with O2 is selected by a gas selector switch, which is effective only in the automatic mode.

Figure 5:
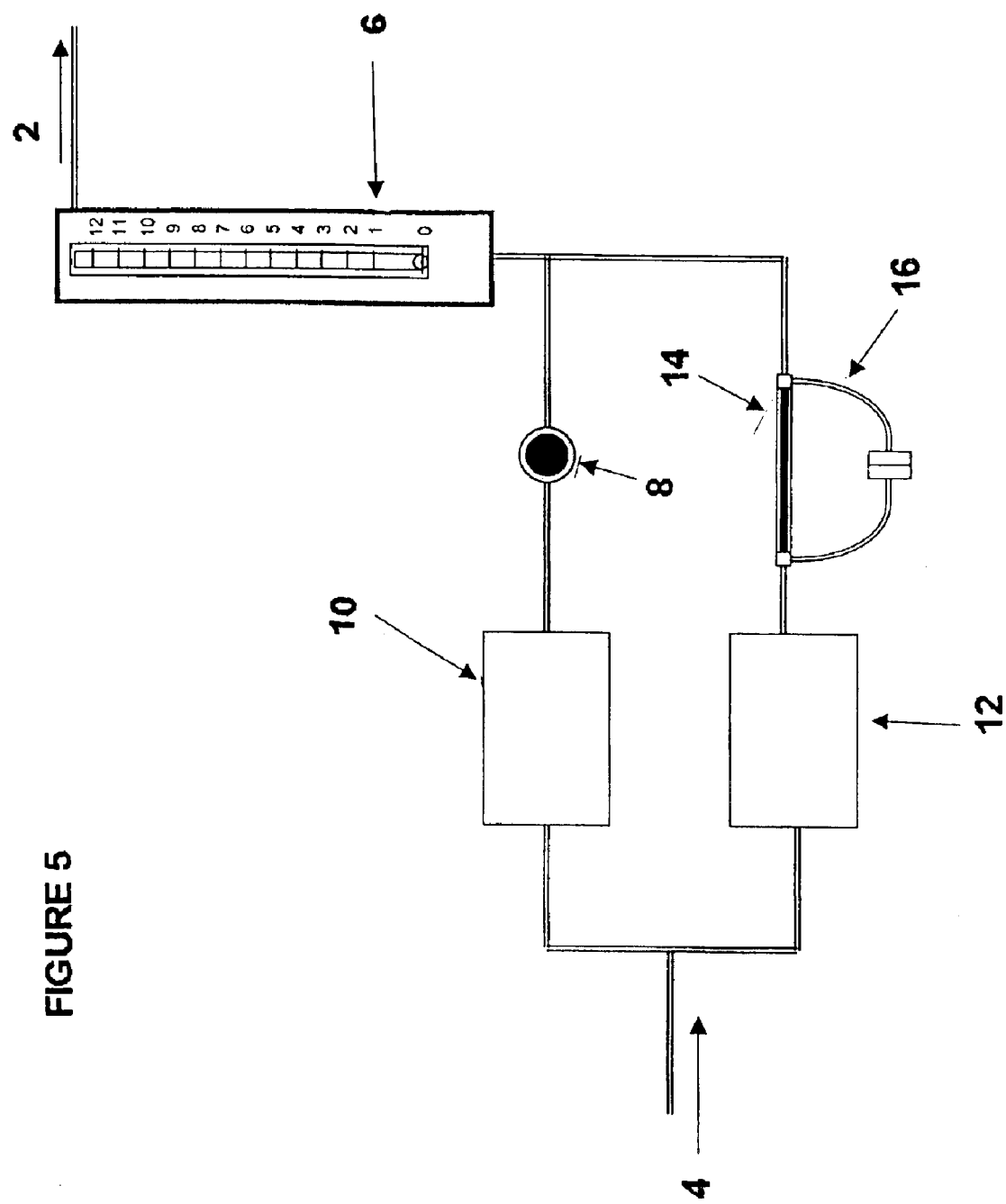
FIG. 5 illustrates gas flow in a control mechanism according to an embodiment of the invention integrated with a parallely connected solenoid valve and conventional needle valve and rotameter.
Figure 6:
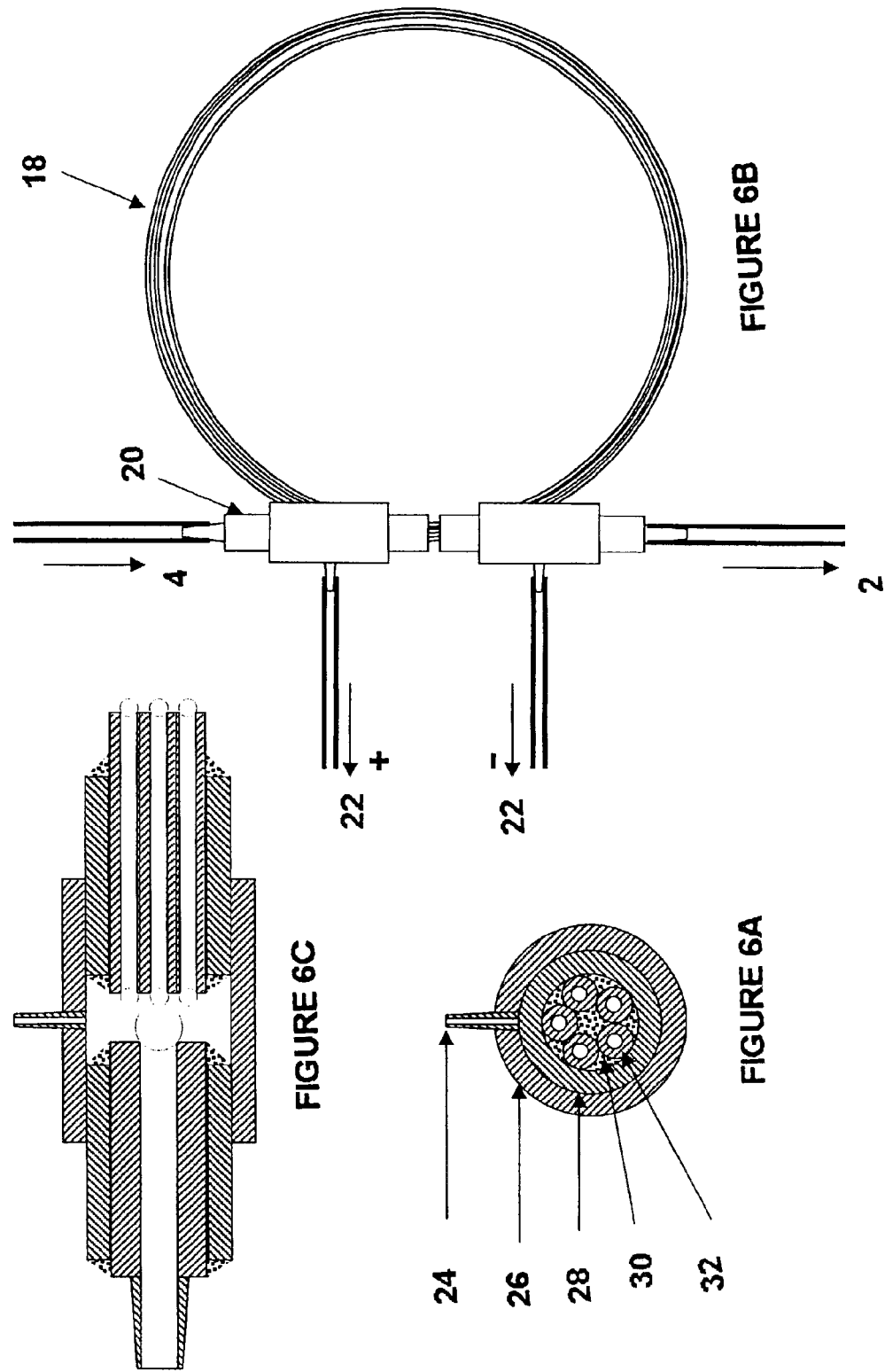
FIG. 6 shows a gas flow resistor and a differential pressure transducer provided in a feed back loop.
Figure 7:
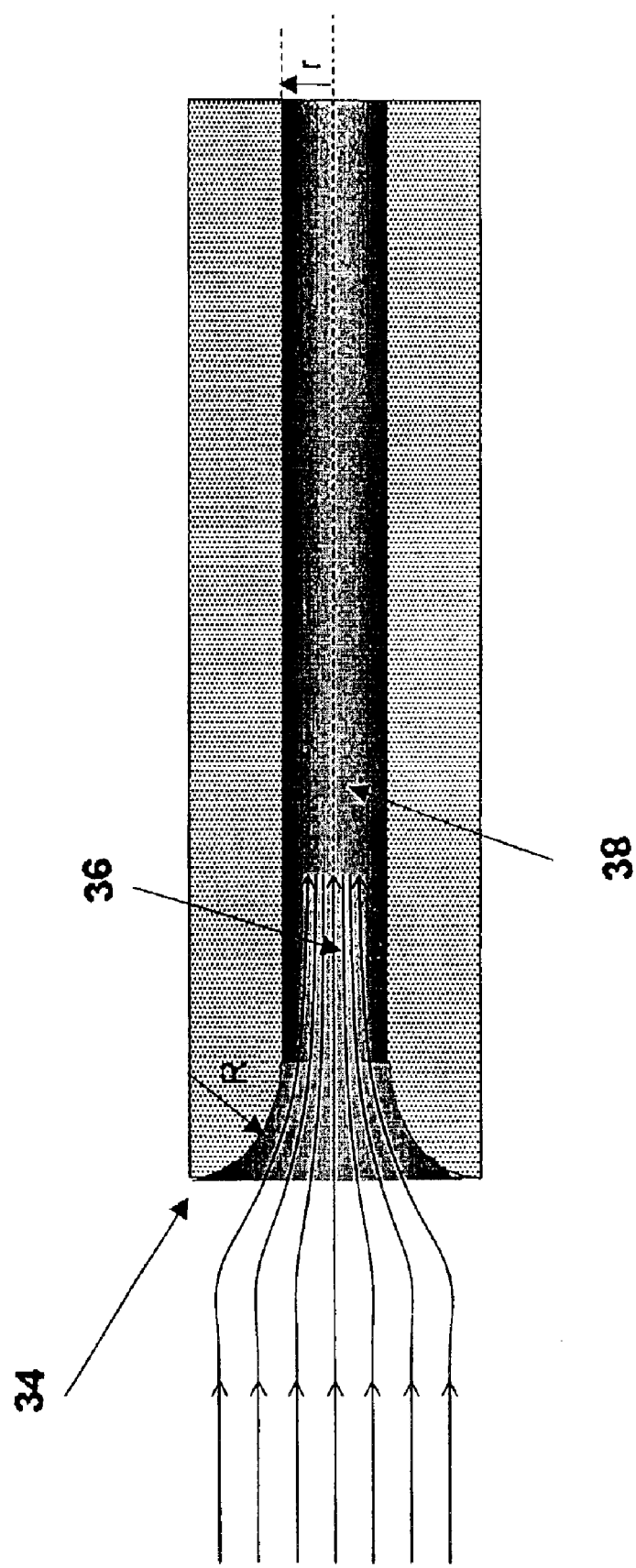
FIG. 7 shows a detailed view of a capillary tube of the flow resistor.
Figure 8C:
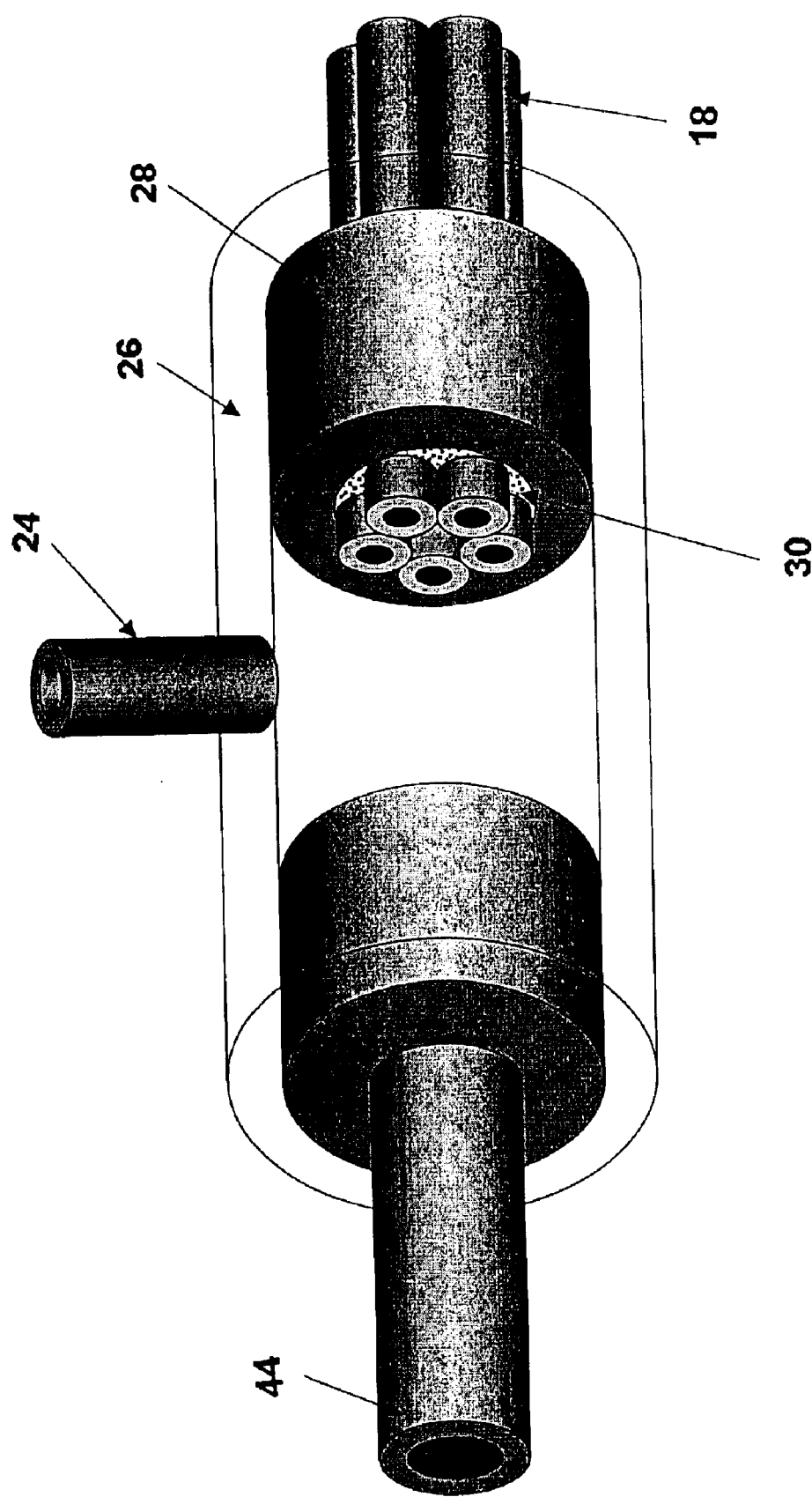

According to one preferred embodiment, as illustrated in FIG. 5, a normally open solenoid valve may be in parallel connection with a normally closed VCO valve so that in case of power failure or such other circumstances the device can be used in the manual mode using traditional needle valves and rotameters for adjusting the gas flows.

Although the gas blender described herein is specifically designed for oxygen (O2), air (AIR) and nitrous oxide (N2O), any other combination of gases could be similarly blended by re-adjusting the potentiometers that set the constants. The blender could also be re-designed to accommodate different flow ranges than those described herein. There are also numerous other applications for which part or all of the circuit described herein could be utilized. For example, a device utilizing a similar flow-control can be devised to sequentially blend O2 and $CO_2$ for use in Functional Magnetic Resonance Imaging (FMRI).

Figure 9:
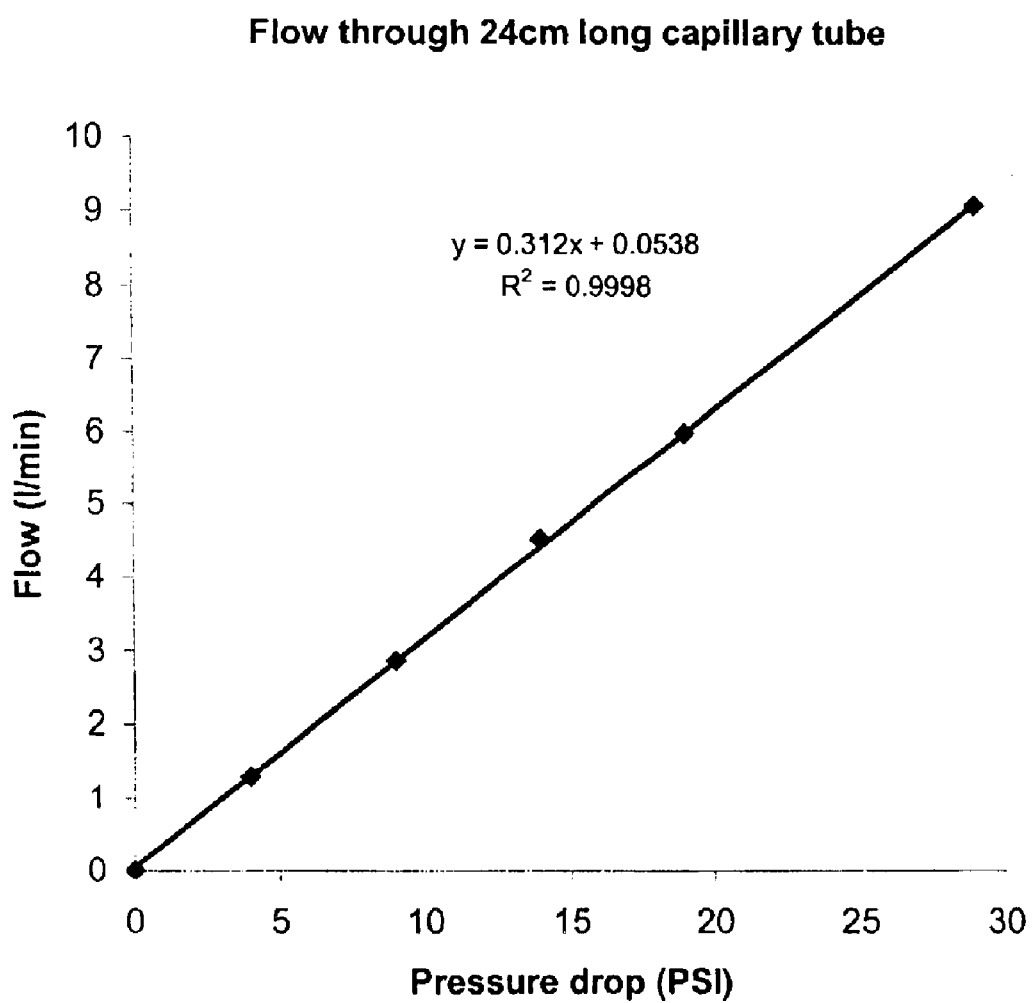
FIG. 9 shows linearity of the flow-pressure relationship in respect of a flow resistor.
Figure 10:
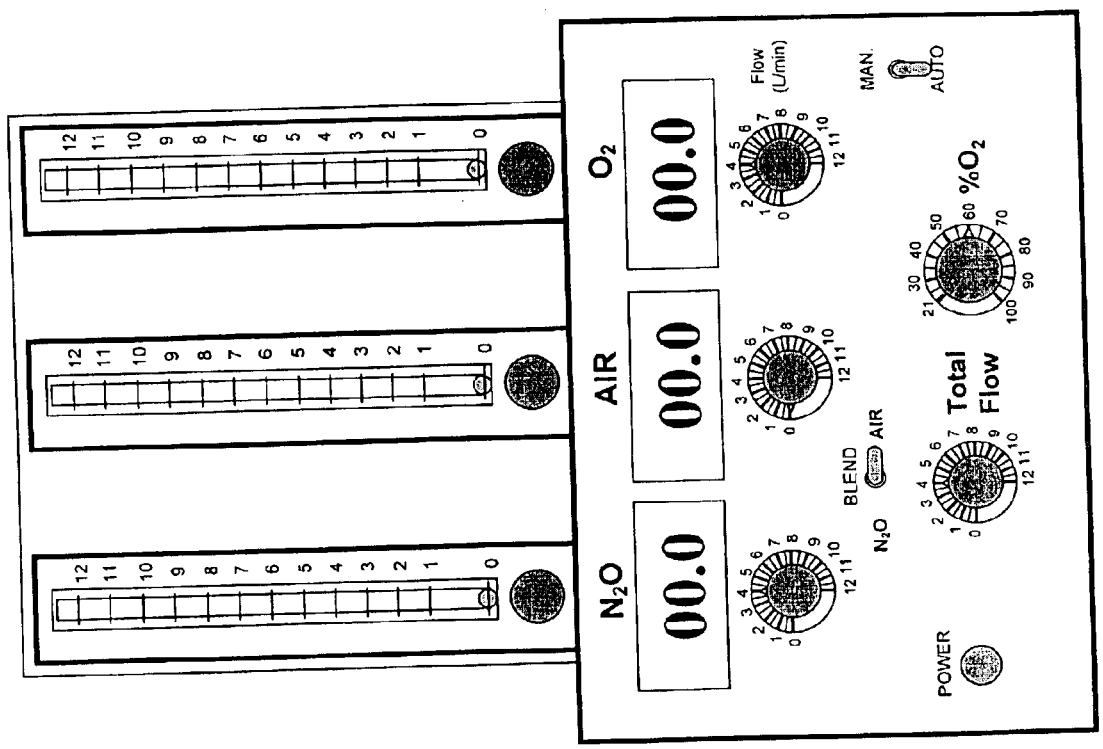
FIG. 10 is the preferred embodiment of the invention.

Each flow resistor may preferably be made from 5 strands of four foot long plastic tubing. The tubing may have an internal diameter of 0.03 in. and an outside diameter of 0.09 in. A typical construction of the flow resistor is shown in FIGS. 6, 7, 8A, 8B and 8C. The length and internal diameter of the tubing were chosen to provide linear flow resistance and low enough resistance to allow about 10 L/min of flow at the minimum source pressure of about 30 PSI. The pressure-flow characteristic of each flow-resistor was investigated by employing a high-resolution rotameter calibrated for each gas. The linearity of the flow-pressure relationship by one of the flow resistors is presented in FIG. 9.

The flared entrance (and identical exit) minimizes turbulent flow entry (and exit). If L>>r, the flow resistance of the tube is given by:

$$R = K*L/r^4$$

Where K=a constant (a function of the tube material and channel wall roughness)

L=the length of the tube and r=the radius of the flow-channel

Although this disclosure has described and illustrated certain preferred embodiments of the invention, it is to be understood that the invention is not restricted to these particular embodiments. Rather, the invention includes all embodiments which are functional, electrical or mechanical equivalents of the specific embodiments and features that have been described and illustrated herein.

What is claimed is:

1. A gas flow control mechanism for a gas blender comprising:
    a voltage sensitive orifice defining a passage for each gas to be controlled and having an inlet port in fluid communication with a gas source and an outlet port in fluid communication with a plenum for mixing at least two gases;
    a gas flow controlling means placed in a feed back loop to adjust at least a parameter or characteristic of a gas flow exiting from the orifice through the outlet port to a preset value;
    the gas flow controlling means comprising:
    a gas flow resistor in fluid communication with the gas exiting from the orifice and adapted to generate an output signal based on a gas flow characteristic; and
    a comparing means, responsive to the gas resistor flow signal, to continuously evaluate and monitor the characteristic of the gas exiting from the orifice, compare the same with the preset value and minimize any difference therebetween by adjusting current supplied to the orifice which in turn adjusts the gas flow therethrough to the preset value by adjusting the passage,
    including a normally open solenoid valve and a needle valve in parallel connection with the orifice and the controlling means, and providing a by-pass connection between the gas source and rotameter connected to the plenum.

2. A control mechanism as claimed in claim 1, wherein the gases are selected from the group consisting of air, oxygen, nitrous oxide, nitric oxide, carbon dioxide, nitrogen and helium.

3. A control mechanism as claimed in claim 2, including a gas selector switch coupled thereto to select the gases to be blended.

4. A control mechanism as claimed in claim 2, wherein the gas flow characteristic includes gas flow rate, concentration or pressure drop or a combination thereof.

5. A control mechanism as claimed in claim 1, wherein the gas flow resistor comprises five strands of about four foot long plastic tubing having an inner diameter of about 0.03 in. and an outer diameter of about 0.09 in.

6. A gas flow control mechanism for a gas blender comprising:
    a voltage sensitive orifice defining a passage for each gas to be controlled and having an inlet in fluid communication with a gas source and an outlet in fluid communication with a plenum for mixing at least two gases;
    a normally open solenoid valve in parallel connection with the orifice to bypass the orifice;
    a gas flow controlling means, placed in a feed back loop, to adjust flow of gas exiting from the orifice to a preset value, comprising:
    a gas flow resistor in fluid communication with the gas exiting from the orifice and adapted to provide a linear flow resistance to the gas traversing therethrough which is low enough to allow sufficient gas flow at a minimum gas source pressure;
    a differential pressure transducer placed in a feed back loop to the flow resistor; and
    a comparator responsive to a signal generated by the transducer and adapted to continuously monitor and compare the existing gas flow with the preset value;
    and an analogue computer to calculate and generate an appropriate voltage signal required to provide the total gas glow and concentration of the preset value; and
    including a needle valve and a rotameter through which the gas exiting from the solenoid valve and the flow resistor traverses before entering the plenum.

7. An electronic gas blender incorporating a gas flow control mechanism as claimed in claim 1.

8. An electronic gas blender incorporating a gas flow control mechanism as claimed in claim 6.

* * * * *